(12) United States Patent
Roseman

(10) Patent No.: US 9,383,359 B2
(45) Date of Patent: *Jul. 5, 2016

(54) ENZYMATIC ACTIVITY BASED-DETECTION

(71) Applicant: Shire Human Genetic Therapies, Inc., Lexington, MA (US)

(72) Inventor: Daniel S. Roseman, Framingham, MA (US)

(73) Assignee: SHIRE HUMAN GENETIC THERAPIES, INC., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/299,358

(22) Filed: Jun. 9, 2014

(65) Prior Publication Data

US 2014/0302531 A1    Oct. 9, 2014

Related U.S. Application Data

(63) Continuation of application No. 13/513,350, filed as application No. PCT/US2010/058454 on Nov. 30, 2010, now Pat. No. 8,778,622.

(60) Provisional application No. 61/265,620, filed on Dec. 1, 2009.

(51) Int. Cl.
G01N 33/573 (2006.01)

(52) U.S. Cl.
CPC ........ *G01N 33/573* (2013.01); *G01N 2333/924* (2013.01)

(58) Field of Classification Search
None
See application file for complete search history.

(56) References Cited

U.S. PATENT DOCUMENTS

| | | |
|---|---|---|
| 6,218,546 B1 | 4/2001 | Watzele et al. |
| 8,778,622 B2 | 7/2014 | Roseman |
| 9,075,057 B2 | 7/2015 | Roseman |
| 2003/0044870 A1 | 3/2003 | Sehr et al. |
| 2006/0057634 A1 | 3/2006 | Rye |
| 2006/0228762 A1 | 10/2006 | Marth et al. |
| 2007/0163960 A1 | 7/2007 | Mattiasson et al. |
| 2007/0184451 A1 | 8/2007 | Byrd et al. |
| 2008/0003211 A1 | 1/2008 | Fogh et al. |
| 2009/0123367 A1 | 5/2009 | Bookbinder et al. |
| 2009/0226968 A1 | 9/2009 | Betenbaugh et al. |
| 2010/0189717 A1 | 7/2010 | Kim et al. |
| 2010/0216163 A1 | 8/2010 | Kuballa et al. |

FOREIGN PATENT DOCUMENTS

| | | |
|---|---|---|
| EP | 1901066 A1 | 3/2008 |
| WO | WO-2008132743 A2 | 11/2008 |
| WO | WO-2009024977 A2 | 2/2009 |
| WO | WO-2011068808 A1 | 6/2011 |

OTHER PUBLICATIONS

Ahmad et al., Immobilization and stabilization of invertase on Cajanus cajan lectin support, Bioresource Technology, 79(2):121-127 (2001).

Bucur et al., Versatile method of cholinesterase immobilisation via affinity bonds using Concanavalin A applied to the construction of a screen-printed biosensor, Biosensors & Bioelectronics, 20(2):217-225 (2004).

European Search Report for EP 10835014.1, dated Apr. 26, 2013 (8 pages).

International Search Report for PCT/US2010/058454, published as WO 2011/068808, dated Feb. 2, 2011 (2 pages).

International Search Report for PCT/US2012/041638, dated Sep. 14, 2012 (3 pages).

Naim et al., Impact of O-Glycosylation on the Function of Human Intestinal Lactase-Phlorizin Hydrolase, The Journal of Biological Chemistry, 267(35):25494-25504 (1992).

Shibuya et al., Fractionation of Sialylated Oligosaccharides, Glycopeptides, and Glycoproteins on Immobilized Elderberry (*Sambucus nigra* L.) Bark Lectin, Archives of Biochemistry and Biophysics, 254(1):1-8(1987).

Shibuya et al., The Elderberry (*Sambucus nigra* L.) Bark Lectin Recognizes the Neu5Ac(α2-6)Gal/GalNAc Sequence, The Journal of Biological Chemistry, 262(4):1596-1601 (1987).

Workman et al., Purification and Properties of β-Glucosidase from Aspergillus terreus, Appl. Environ. Microbiol., 44(6):1289-1295 (1982).

Written Opinion for PCT/US2010/058454, 9 pages (Feb. 2, 2011).
Written Opinion for PCT/US2012/041638, 9 pages (Sep. 14, 2012).

*Primary Examiner* — Brian J Gangle
(74) *Attorney, Agent, or Firm* — Choate, Hall & Stewart LLP; Charles E. Lyon; Rolando Medina

(57) ABSTRACT

Disclosed herein are methods and kits which are useful for detecting presence of an enzyme in a test sample based upon the intrinsic enzymatic activity of such test sample. The present invention provides the ability to evaluate cell culture conditions and optimize the desired glycoform content of recombinantly prepared enzymes.

42 Claims, 6 Drawing Sheets

ENZYMATIC ACTIVITY BASED-DETECTION

RELATED APPLICATION(S)

This application is a continuation of U.S. application Ser. No. 13/513,350, filed Jul. 31, 2012, now U.S. Pat. No. 8,778,622, which was the National Stage of International Application No. PCT/US2010/058454, filed Nov. 30, 2010, which claims the benefit of U.S. Provisional Application No. 61/265,620, filed Dec. 1, 2009, the entire teachings of which are incorporated herein by reference.

BACKGROUND OF THE INVENTION

Glycoproteins and glycoenzymes are proteins that contain a post-translational modification wherein oligosaccharide chains (known as glycans) are covalently attached to the protein's or enzyme's polypeptide side chains. This process, which is known as glycosylation, is one of the most abundant protein post-translational modifications. It is estimated that more than half of all cellular and secretory proteins are glycosylated. (Apweiler et al., 1999, Biochim. Biophys. Acta 1473: 4-8). Although mammalian glycoprotein oligosaccharides, for example, are constructed from a limited number of monosaccharides, their structural diversity is vast due to complex branching patterns. Glycoproteins, therefore, represent a diverse group of modifications, and variants of glycoproteins or glycoenzymes (which are known as glycoforms) can impact protein or enzyme activity or function. The ability to evaluate and distinguish specific glycan structures during the preparation of recombinant enzymes can accordingly provide valuable information relating to recombinant enzyme development and further optimization of the desired glycoform content of such recombinant enzymes.

Conventional techniques which are routinely employed for glycoprotein and glycoenzyme analysis include mass spectrometry, lectin affinity chromatography and western blotting. Although these conventional methods of analysis are generally accurate, they are time consuming, require purification of the protein, and some, such as mass spectrometry, require specific expertise and are technically challenging. (Wang et al., 2006, Glycobiol. Epub.; Qiu et al., 2005, Anal, Chem. 77:2802-2809; Qiu et al., 2005, Anal Chem. 77:7225-7231; Novotny et al., 2005, J. Sep. Sci. 28:1956-1968). Accordingly, these issues make the routine use of such technologies impractical for high-throughput monitoring of enzyme glycosylation, especially during process development and manufacturing. Such technologies may also present challenges to a typical research laboratory attempting to study the impact of glycosylation on the biological properties of proteins and enzymes.

Traditionally, to provide a quantitative assessment of the glycan structure of a glycoprotein, lectin array platforms required the use of either a reliable glycoprotein specific antibody or direct conjugation of a fluorescent dye to the glycoprotein. These antibody-based detection strategies are limited by the fact that antibody recognition of a given glycoprotein or glycoenzyme may be blocked or reduced depending on the type of glycan structure linked to the protein or enzyme, thereby allowing recognition of only a subset of the total glycoprotein pool and not the range of potential glycan structures. Antibody-based recognition may also require multiple binding and wash steps, which can add time and complexity to an analysis. While these problems can be circumvented using direct labeling of the glycoprotein, direct labeling remains limited to pure preparations of material, since the labeling techniques do not discriminate among proteins. Accordingly, direct labeling cannot be used for "dirty" or in-process samples. The utility of currently available methods for glycan analysis may be further limited because large quantities of highly purified materials may not readily be available from in-process test samples. Furthermore, purified material may only represent a subset of the initial glycoform population because the purification process is typically selective for certain glycan structures.

The identification and characterization of protein and enzyme glycoforms is essential in the development of recombinant proteins and enzymes. For example, glycosylation of recombinantly-prepared enzymes must frequently be controlled during production to maintain the efficacy and safety of such recombinant enzymes, and cell culture conditions can affect the carbohydrate structures of glycoproteins. Further understanding of cell culture conditions that can impact the carbohydrate structures of recombinantly-prepared proteins or enzymes is also important for the development of an effective and robust recombinant production process.

Improved methods and compositions are needed for the rapid, direct and systematic identification and evaluation of the glycan structures of a given protein or enzyme and their variant glycoforms. High throughput methods and compositions that are capable of efficiently assessing and distinguishing among a diverse range of glycosylation states or glycoforms would provide valuable information for drug discovery and disease therapeutics, provide valuable tools regarding ongoing research, and facilitate the optimization of recombinant production processes.

SUMMARY OF THE INVENTION

The present invention provides novel methods, assays and compositions for the accurate and rapid identification and/or detection of various glycoforms of enzymes. In particular, the present invention relies upon the intrinsic activity of the enzyme of interest to detect such enzyme's presence in a test sample. The methods, assays and compositions disclosed herein also provide novel strategies for analyzing the different glycoforms of unpurified proteins or enzymes in cell culture harvest test samples. Furthermore, the present invention provides the ability to detect and distinguish among different glycoforms or glycovariants of an enzyme in upstream harvest test samples, thereby facilitating the optimization of cell culture conditions that affect the viable glycoform content of recombinantly-prepared enzymes. The methods and kits of the present invention are advantageously capable of determining the presence of glycosylated enzymes in a test sample irrespective of the presence of additional cellular proteins, biological materials or other contaminants which may be present in that test sample.

Disclosed herein are methods for detecting the presence of an enzyme (e.g., a recombinantly prepared enzyme) in a test sample, such methods comprising contacting the test sample with at least one capture agent (e.g., a lectin) under conditions appropriate for binding of glycosylated enzyme in the test sample to the capture agent, wherein upon binding of glycosylated enzyme to capture agent a complex is formed which is referred to herein as a "bound enzyme." Such methods also contemplate separation of the test sample from the bound enzyme produced by the previous step (e.g., using routine means such as washing) followed by detection of the intrinsic enzymatic activity of the bound enzyme. The presence of intrinsic enzymatic activity is indicative of the presence of enzyme in the test sample.

Also disclosed are methods for detecting the presence of an enzyme (e.g., a recombinantly prepared enzyme) in a test sample, wherein such methods comprise the steps of contacting a test sample with at least one capture agent (e.g., a lectin) under conditions appropriate for binding of the glycosylated enzyme, and thereby forming a bound enzyme when glycosylated enzyme is present. The methods of the present invention also contemplate separating the bound enzyme from the test sample and contacting the bound enzyme with at least one substrate. In accordance with the present invention, the presence of intrinsic enzymatic activity of such bound enzyme is indicative of the presence of the glycosylated enzyme of interest in the test sample. Conversely, the absence of intrinsic enzymatic activity is indicative of the absence of the glycosylated enzyme of interest in the test sample. The methods disclosed herein provide the ability to optimize the desired glycoform content of one or more recombinant enzymes during recombinant preparation.

In one embodiment, the methods of the present invention further comprise the step of fixing a capture agent (e.g., one or more lectins) onto a solid support (e.g., a microtiter plate or one or more populations of beads). In one embodiment, such solid support may comprise or be coated with avidin, streptavidin or a metal chelator such as a nickel chelate. If such solid support comprises avidin or streptavidin, the use of derivatized lectins (e.g., biotinylated lectins) are preferred. If such solid support comprises a nickel chelate, the use of six consecutive histidine residues (6His) as an affinity tag is preferred. For example, a capture agent may be a fusion protein which includes one or more histidine (HIS) residues (e.g., at least one, at least two, at least three, at least four, at least five, at least six, at least eight, at least ten, at least twelve, at least twenty, at least twenty five or more HIS residues) at either the N- or C-terminus as an affinity tag to facilitate fixing of that capture agent (i.e., the fusion protein) to a solid support.

In one embodiment of the present invention the capture agent comprises one or more lectins. The lectins contemplated by the methods, assays and kits of the present invention include, for example, concanavalin A, wheat germ agglutinin, Jacalin, lentil lectin, peanut lectin, *lens culinaris* agglutinin, *Griffonia* (*Bandeiraea*) *simplicifolia* lectin II, *Aleuria aurantia* lectin, *hippeastrum* hybrid lectin, *sambucus nigra* lectin, *maackia amurensis* lectin II, *ulex europaeus* agglutinin I, *lotus tetragonolobus* lectin, *galanthus nivalis* lectin, *euonymus europaeus* lectin, *ricinus communis* agglutinin I, and any combinations thereof.

In another embodiment of the present invention the capture agent comprises a receptor, or a binding fragment thereof, known to demonstrate affinity for or otherwise bind to one or more particular glycoforms of an enzyme. For example, mannose-6-phosphate (M6P) binds the mannose-6-phophate receptor (M6PR), and in one embodiment a recombinant fusion protein comprising the M6PR or a binding domain thereof (e.g., M6PR domain 9) may serve as the capture agent. In one embodiment, the recombinant fusion protein capture agent may also comprise one or more histidine residues (e.g., 6His) to facilitate purification, capture and/or fixing of the capture agent to a solid support. In one embodiment of the present invention, the capture agent comprises the fusion protein M6PR(D9)6His.

Also disclosed is a method of determining the intrinsic enzymatic activity of the bound enzyme by contacting such bound enzyme with a substrate, for example, a substrate which has known reactivity with the enzyme suspected of being present in the test sample. In accordance with the methods of the present invention, the presence of intrinsic enzymatic activity is indicative of the presence of enzyme in the test sample. Alternatively, the absence of intrinsic enzymatic activity may be indicative of the absence of such enzyme in the test sample.

In one embodiment, the methods, assays and kits of the present invention contemplate determining intrinsic enzymatic activity by contacting bound enzyme with a substrate which is known to predictably react with the enzyme of interest. For example, if the enzyme is agalsidase alfa the selected substrate may be 4-nitrophenyl-α-D-galaetopyranoside, if the enzyme is galactocerebrosidase the selected substrate may be 4-nitrophenyl-β-D-galactopyranoside, and if the enzyme is aryl sulfatase A the selected substrate may be p-nitrocatechol sulfate. The presence or absence of intrinsic enzymatic activity of the bound enzyme may be determined by means which are known to those of ordinary skill in the art. In one embodiment a quantitative assessment of the depletion of substrate and/or the conversion of substrate to product may be indicative of intrinsic enzymatic activity. For example, in one embodiment substrate depletion of about 5%, 10%, 20%, 30%, 40%, 50% or more, or preferably about 55%, 60%, 65%, 70%, 75%, 80%, 85%, 90%, 95%, 99% or more relative to the amount of substrate introduced may be indicative of intrinsic enzymatic activity. Alternatively, following contacting an enzyme with a substrate, a relative increase in the formation of a product, or the conversion of substrate to product, in each case of about 5%, 10%, 20%, 30%, 40%, 50% or more, or preferably about 55%, 60%, 65%, 70%, 75%, 80%, 85%, 90%, 95%, 99%, 100% or more, may be indicative of intrinsic enzymatic activity. Substrates contemplated by the present invention include, for example, 4-nitrophenyl-α-D-galactopyranoside, 4-nitrophenyl-β-D-galactopyranoside and para-nitrocatechol sulfate.

Also disclosed herein are kits which are useful for detecting the presence of glycosylated enzymes (e.g., a recombinantly prepared glycosylated enzyme) in a test sample. Such kits comprise at least one capture agent (e.g., a lectin) capable of binding a glycosylated enzyme, and at least one substrate which is reactive with such glycosylated enzyme. In one embodiment the kits of the present invention comprise a solid support (e.g., a multiple well microtiter plate), onto which may be fixed a capture agent (e.g., the lectin *sambucus nigra* agglutinin).

In one embodiment, the kits of the present invention comprise a capture agent which is known to bind or demonstrate affinity for the targeted glycoform of the enzyme of interest (e.g., the M6PR(D9)6His fusion protein), and a substrate which is known to react with such enzyme. In one embodiment, such kits may also comprise a means of separating or removing excess test sample from the solid support, for example by washing, or other routine means available to one of ordinary skill in the art.

Also contemplated are kits which are capable of identifying multiple glycosylated enzymes and multiple glycoforms of those enzymes in the same test sample. For example, the kits of the present invention may comprise multiple capture agents (e.g., lectins) fixed onto one or more solid supports (e.g., populations of inert beads), and thus provide the capability of binding to multiple glycoforms of one or more enzymes in the same test sample. The kits of the present invention may also comprise one or more substrates (each of which correspond to a particular enzyme whose presence is suspected in a test sample) to determine such enzymes' intrinsic enzymatic activities. Preferably, the selected substrate is known to predictably bind to, or react with, the enzyme of interest. For example, if the enzyme is agalsidase alfa the selected substrate may be 4-nitrophenyl-α-D-galactopyranoside, if the enzyme is galactocerebrosidase the selected substrate may be 4-nitrophenyl-β-D-galactopyranoside, and if the enzyme is aryl sulfatase A the selected substrate may be p-nitrocatechol sulfate. Based upon the binding specificity or reactivity of the test sample with the substrate, one having ordinary skill in the art may use routine means to assess the presence or absence of intrinsic enzymatic activity (e.g., by quantitatively determining substrate depletion and/or the conversion of substrate to product).

The above discussed and many other features and attendant advantages of the present invention will become better understood by reference to the following detailed description of the invention when taken in conjunction with the accompanying examples.

DETAILED DESCRIPTION OF THE INVENTION

Figure 1:
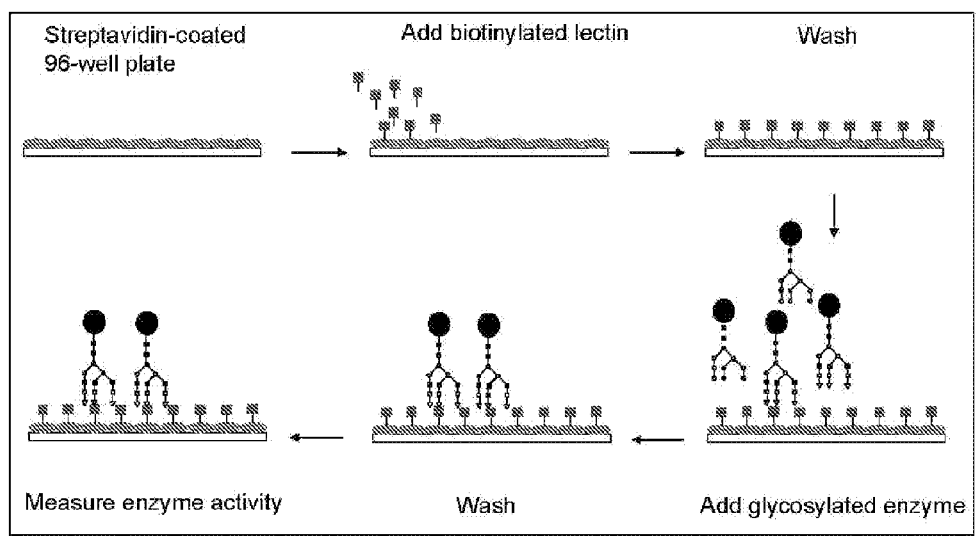
FIG. 1 schematically illustrates one embodiment of the present invention in which biotinylated lectins are bound to streptavidin-coated plates, to which are added test sample materials containing different preparations of a given glycosylated enzyme which are allowed to bind. Unbound test sample materials are then removed by a wash step, and specific detection of the bound enzyme is performed by the addition of the appropriate substrate and assay conditions.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and are not intended to be limiting.

Disclosed herein are high throughput methods, assays, kits and compositions for screening complex test samples for the presence of glycosylated enzymes of interest or for determining changes in glycosylation of such enzymes. Also disclosed herein are methods and kits which are capable of detecting the intrinsic activity of an enzyme in a test sample as a means of determining the presence of that enzyme in the test sample. For example, in one aspect the present invention relies upon the intrinsic enzymatic activity of an enzyme to detect its presence in a test sample. This is in contrast to antibody-based detection schemes which can be negatively influenced by changes in glycosylation, for example by hindrance of antibody recognition of the enzyme. The invention provides the ability to study cell culture conditions and optimize the desired glycoform content of biological samples, and in particular of recombinantly prepared enzymes.

In the context of the present invention, the term "glycan" refers to the carbohydrate portion of a glycoprotein or glycoenzyme. Generally, glycans tend to be oligosaccharides or polysaccharides. The terms "glycoform" and "glycovariant" refer to an isoform of a protein or enzyme with a unique primary, secondary, tertiary, and/or quaternary structure based upon the number and/or structure of the glycans attached to such protein or enzyme. It is often the case that a single glycoprotein may have over a thousand different glycoforms or glycovariants, all of which are based on differences in the glycan portion or glycosylation pattern of the glycoprotein. The term "glycosylation" refers to the process or result of adding saccharides to proteins and thus forming "glycoproteins". Glycosylation includes both N-linked glycosylation to the amide nitrogen of asparagine side chains, and O-linked glycosylation to the hydroxy oxygen of serine and threonine side chains.

The term "test sample" is used in its broadest sense and means any preparation, preferably obtained from biological media or materials, including biologically or recombinantly derived media which may contain, among other things, naturally occurring or recombinantly prepared peptides, polypeptides or proteins, enzymes, lipid or carbohydrate molecules, or glycosylated proteins or enzymes, or other samples obtained from a recombinant media, including any fractions thereof. The test samples contemplated by the present invention are preferably obtained from in-process or "dirty" biological systems, for example, those obtained during the preparation of a recombinant enzyme.

As used herein, the term "solid support" refers to any material that provides a solid or semi-solid structure with or upon which another material can be attached or fixed. Such materials include smooth supports (e.g., metal, glass, plastic, silicon, and ceramic surfaces) as well as textured and porous materials. Such materials also include, but are not limited to, gels, rubbers, polymers, dendrimers and other non-rigid materials. Solid supports need not be flat. Supports include any type of shape including spherical shapes (e.g., beads) and may include multiple well microtiter plates, and may optionally be coated with proteins, resins or other similar reagents, such as for example, avidin, streptavidin, metal ions or chelates (e.g., a nickel chelate).

The present invention contemplates the use of one or more capture agents to facilitate capture, immobilization or fixing of the glycosylated enzyme of interest (e.g., capture or fixing of one or more glycosylated enzymes onto a solid support). As used herein, the phrase "capture agent" refers to a compound or a material which demonstrates affinity for or is capable of conjugating or associating with one or more specific saccharide or carbohydrate moieties. Preferably the selected capture agent demonstrates specific or discriminatory affinity for one saccharide moiety, such that the capture agent will only bind one particular glycoform of a given enzyme. In a preferred embodiment of the present invention, the capture agent is selected based upon its specific affinity to one or more glycan structures. When contacted with such a glycan structure or glycosylated enzyme in accordance with the present invention the capture agent will form a complex referred to herein as a "bound enzyme."

In one embodiment of the present invention, the capture agent is a lectin. Lectins represent a family of saccharide-recognizing proteins which are classified based upon the specificity of the mono-saccharide groups for which they exhibit the highest affinities. Lectins are non-enzymatic and non-immune in nature and are capable of binding to the saccharide moiety of a glycoprotein or glycoenzyme. As used herein, the term "lectin" refers to a non-antibody compound which binds to a specific carbohydrate structure or target, such as for example, a glycosylated biological or recombinantly derived molecule or a glycosylated enzyme, to form a larger complex. When used in accordance with the present invention, one or more lectins are selected based upon such lectins' affinity for a specific glycan structure or a glycosylated enzyme. Preferably, the lectin is selected for its biological affinity for a specific glycan structure, or for a targeted glycosylated enzyme of interest whose presence is suspected in a test sample. In a preferred embodiment the methods and kits of the present invention contemplate the selection of lectins which are capable of recognizing and discriminatorily binding to specific glycoforms of an enzyme. For example, if the enzyme of interest in a selected test sample is a glycosylated form of the enzyme agalsidase alpha, then a lectin with affinity for that enzyme (such as, for example, the lectin concanavalin A) would be preferentially incorporated into the assays, kits and methods of the present invention.

The lectin's biological affinity for a specific glycan structure can be exploited in accordance with the present invention to isolate glycosylated enzymes or specific glycoforms of an enzyme in a test sample. Numerous lectins are commercially available, and information on the binding specificity of a given lectin can be obtained from the manufacturer or as is described herein. Representative lectins include, but are not limited to, concanavalin A (Con A), wheat germ agglutinin (WGA), Jacalin, lentil lectin (LCA), peanut lectin (PNA). *Lens culinaris* agglutinin (LCA), *Griffonia* (*Bandeiraea*) *simplicifolia* lectin II (GSLII) *Aleuria aurantia* Lectin (AAL), *Hippeastrum* hybrid lectin (HHL, AL), *Sambucus nigra* lectin (SNA), *Maackia amurensis* lectin II (MAL II), *Ulex europaeus* agglutinin I (UEA I), *Lotus tetragonolobus* lectin (LTL), *Galanthus nivalis* lectin (GNL), *Euonymus europaeus* lectin (EEL), *Ricinus communis* agglutinin I (RCA), or combinations thereof.

In an alternative embodiment of the present invention, the capture agent may comprise one or more fusion proteins, wherein such fusion proteins preferably comprise one or more binding domains which are capable of recognizing and binding to one or more specific saccharide or carbohydrate moieties of a glycosylated enzyme. For example the mannose-6-phosphate receptor (M6PR) is capable of binding mannose-6-phophate (M6P). The M6PR is approximately 300 kDa and consists of approximately 15 extracellular domains. In one embodiment of the invention a fusion protein capture agent comprises one or more M6PR binding domains (e.g., M6PR domains 1, 3, 5, 9 and/or 11) which demonstrate affinity for M6P and/or other glycoforms of interest. Preferably, the selected binding domain demonstrates high affinity for the saccharide or carbohydrate moieties of interest (e.g., M6PR domains 3 and 9 correspond to high affinity M6P binding sites). The recombinant fusion protein capture agents of the present invention may optionally comprise one or more regions or tags to facilitate purification, isolation or fixation of the capture agent (e.g., fixation to a solid support). For example, in one embodiment of the present invention six histidine residues (6His) may be linked to a M6PR binding domain to facilitate the purification, capture or fixation of the capture agent to a solid support (e.g., a nickel chelate-coated 96-well plate). The fusion protein capture agents of the present invention may further comprise one or more linker or spacer groups. In one embodiment of the present invention, the capture agent comprises the fusion protein M6PR(D9) 6His which may be expressed, for example, in HT1080 cells and purified using nickel chelate affinity chromatography.

The present invention contemplates that capture agents (e.g., lectins) may optionally be fixed onto any portion of a solid support (e.g., may be attached to an interior portion of a porous solid support material). As used herein, the terms "fixed", "affixed" and "fixing" mean bound, adhered to or immobilized, for example, physically and/or chemically. As the term specifically relates to a solid support and a capture agent, "fixed" or "affixed" mean that the capture agent remains bound to, or immobilized on, a solid support despite being subjected to wash conditions or conditions which may alter such physical or chemical bonds. Fixing may be, for example, spontaneous or result from an additional step. Exemplary methods of fixing include evaporation (for example, removal of volatile solvent), cooling (for example, resulting in a phase change from liquid to solid, or viscosity thickening), and curing (for example, polymerization and/or crosslinking). The present invention contemplates the use of derivatized lectins as capture agents to enhance the ability to fix a lectin onto a solid support. For example, biotinylated lectins demonstrate an enhanced ability to affix onto a solid support coated with avidin or streptavidin, (e.g., a 96 well plate, optionally coated with avidin or streptavidin) and the use of such derivatized lectins are contemplated by the present invention, (Thompson et al, 1989, Clin. Chim. Acta 180(3):277-84). Other useful derivatives include, but are not limited to, labels, fluorescent probes such as rhodamine, or FITC, radioactive labels, electroactive labels, affinity tags (e.g., 6His) that can conjugate with secondary labels, oligonucleotides for PCR amplification, such as green fluorescent protein or luciferase, chromogenic peptides, and any combinations thereof.

In one embodiment of the present invention an array of biotinylated lectins of differing carbohydrate specificities is immobilized directly onto wells of streptavidin coated 96-well microtiter plates as illustrated in FIG. 1. Test samples containing different preparations of a given glycosylated enzyme (e.g., aryl sulfatase A (ARSA), agalsidase alfa, galactocerebrosidase (GalC) or heparin N-sulfatase (HNS)) are allowed to bind and unbound material removed by a wash step.

One aspect of the present invention involves the identification and selection of capture agents (e.g., lectins) that demonstrate an affinity for a glycan structure of interest, or for specific glycoforms of a recombinantly prepared enzyme and a determination that such lectins are suitable for binding to the specific enzyme glycoform of interest. The particular capture agent selected for use in the present invention is generally determined based on the ability of such capture agent to bind to a specific glycosylation structure, such as mannose-6- phosphate, fucose, sialic acid, galactose, or any other specific sugar. In some cases, selection of a capture agent is based on the glycosylation of the enzyme targeted for capture. In other cases, the binding agents are selected based on empirical determinations such as high throughput assays. For example, a capture agent can be bound to a solid support and the ability of the capture agent to bind a desired fraction of glycosylated enzyme(s) may be determined by using means known to one of ordinary skill in the art (e.g., an ELISA assay). A capture agent for use in the methods, assays and kits of the present invention may then be selected based upon such capture agent's ability to bind the glycan structure of interest or a particular glycoform of an enzyme in a test sample. A suitable capture agent for use in the present invention may then be used to identify the presence or absence of a glycosylated enzyme of interest in a test sample. For example, such capture agents may be used to determine the presence of a particular glycoform of a recombinant enzyme in a harvest test sample extracted from various stages in the development process of that recombinant enzyme.

A determination of the binding affinity of a particular capture agent for a glycosylated enzyme of interest may be performed by fixing a panel of labeled capture agents (e.g., biotinylated lectins) on a solid support (e.g., a 96 well plate, optionally coated with avidin or streptavidin). The capture agent panel is then contacted with a test sample suspected of containing the glycosylated enzyme of interest. In the presence of the glycosylated enzyme of interest, such enzyme will bind to the capture agent panel and form a bound enzyme complex.

In general, the compositions of the present invention are prepared by attaching (e.g., covalently attaching) at least two (e.g., at least three, at least four, at least five or more) capture agents onto a solid support or to a molecule that is attached to a solid support (e.g., avidin, streptavidin or a nickel chelate). One embodiment of the present invention contemplates the selection of multiple capture agents which are prepared by physically mixing at least two (e.g., three, four, five, or more) distinct capture agents and that are subsequently fixed on one or more solid supports. The amount of a specific capture agent that is selected may be based on the test sample concentration and the approximate concentration of the target glycoenzyme of interest in that test sample. In general, the amount of the capture agent fixed onto a solid support to be contacted by a test sample is in excess of at least about 50% (e.g., at least 75% or at least 100%) of the amount of the portion of the target glycosylated enzyme predicted to bind to the capture agent. Alternatively, capture agents are immobilized on a solid support at various capture agent/solid support ratios or concentrations. The binding capacity of the capture agent/solid support composition may then be determined, or the amount of a test sample that can be loaded without saturating the solid support may be determined. In general, it is desirable that the amount of capture agent fixed on the solid support is at least two-fold in excess of the amount of glycosylated enzyme that is to be bound (e.g., a ten-fold excess or a 100-fold excess).

The invention provides, in part, a capture agent (e.g., multi-capture agent) affinity kit for use in practicing the methods and assays of the invention. The kits of the present invention may include, for example, at least two capture agents (e.g., lectins) bound to one or more solid supports. Examples of such solid supports include, without limitation, one or more beads or microbeads composed of silica, agarose, or a polymer, a plate (e.g., a microtiter plate), a slide (e.g., glass or polymer slide), a nanowell plate, or polyethylene glycol or other soluble polymer that can be precipitated or isolated by some other physical process to which a capture agent is bound. The capture agents used in the invention can be attached to the solid support directly or indirectly (e.g., using an antibody or biotin) using methods known to those of ordinary skill in the art, (e.g., using aldehyde functionalized resins or linkers such as cyanogen bromide, carbonyl diimidazole glutaraldehyde, epoxy, periodate, or bisoxirane) (Harris et al, 1989, In Protein Purification Methods. A Practical Approach, IRL Press, New York, N.Y.). In the case of particulate supports such as agarose beads, a mixture of capture agents (e.g., lectins) may be fixed onto a single bead, or in certain embodiments, a single type of capture agent is attached to each bead and the mixture of capture agents used in the composition is prepared by mixing at least two of these bead populations. Alternatively the capture agent may be attached to a restricted access media for the purposes of selecting glycosylated enzymes of different molecular weight ranges.

The present invention further contemplates the binding of glycosylated enzymes present in a selected test sample, (e.g., recombinant enzymes) to the capture agent to produce a bound enzyme. As used herein, a glycosylated enzyme is said to have "bound" its respective capture agent when it has associated with the capture agent through a non-random chemical or physical interaction. The terms "bind" or "bound" mean the coupling of one molecule (e.g., a glycosylated enzyme, such as the enzymes arylsulfatase A, agalsidase alfa and galactocerebrosidase) to another molecule (e.g., a lectin, such as the lectins concanavalin A, *sambucus nigra* agglutinin and wheat germ agglutinin). Binding of an enzyme to a capture agent is preferably achieved under conditions suitable for such binding to occur. Binding may be achieved by chemical means (e.g., covalent or non-covalent in nature); however in a preferred embodiment, binding of the capture agent to the glycosylated enzyme of interest in the test sample is achieved by way of a covalent bond. Such binding need not be covalent or permanent. Following contact of the capture agent with the test sample, the test sample is preferably contacted with a wash solution such that the excess or unbound test sample fraction can be separated or removed, and if appropriate collected for analysis.

Generally, the specificity in the detection of the bound enzyme will be performed by determining the enzyme's activity via addition of appropriate substrate and assay conditions as demonstrated in FIG. 1. The signal determined for a given capture agent (e.g., a lectin) coupled with the known specificity of that capture agent will allow for a fast, high throughput, semi-quantitative structure assessment of the glycoforms present in the test sample. To determine the presence of the glycosylated enzyme of interest in a test sample, the bound enzyme fraction is contacted with a substrate. As used herein, the term "contact" means that two or more substances (e.g., a bound enzyme and a substrate) are sufficiently close to each other such that the two or more substances interact or react (e.g., chemically or biologically) with one another. The term "substrate" refers to a molecule, complex, material, substance or reactant with which an enzyme reacts (e.g., chemically or biologically), acts or binds. In particular, the substrates of the present invention may demonstrate a physiological, biological and/or chemical affinity for, or be able to be acted upon, by a corresponding enzyme. A substrate useful in the methods of the invention can be native or modified. Modified substrates useful in the invention retain the ability to be acted upon by the corresponding enzyme. Exemplary modifications suitable for substrates include, for example, labeling to confirm the presence or absence of intrinsic enzymatic activity. One aspect of the present invention contemplates the selection of substrates based upon its ability to interact with, or bind to the enzyme of interest in a predictable and repeatable fashion. For example, a substrate with which an enzyme is known to react would be preferable. Once a suitable substrate has been identified, that substrate is preferably contacted with the bound enzyme and the presence or absence of the anticipated reaction or interaction is assessed.

Based upon the known intrinsic enzymatic activity of the enzyme, in the presence of the appropriate substrate the bound enzyme would be expected to react, and accordingly signal the presence of that enzyme in the test sample. For example, the product of an enzyme reaction with a substrate (e.g., a molecular entity that is produced or liberated as a result of enzyme acting on substrate) may provide a measurable signal indicative of the presence of enzyme in the test sample, and that correlates with the presence or amount of intrinsic enzymatic activity in the test sample. Alternatively, quantitative assessments of substrate binding or depletion and/or assessments of the conversion of substrate to product may be performed and used as a surrogate marker of intrinsic enzymatic activity. Examples of suitable substrates for use in the present invention include 4-nitrophenyl-α-D-galactopyranoside, 4-nitrophenyl-β-D-galactopyranoside and para-nitrocatechol sulfate.

Selection of the appropriate enzyme substrate and the subsequent determination of intrinsic enzymatic activity require an understanding of enzyme kinetics and in particular the catalytic properties of the enzyme(s) being evaluated. For example, enzymatic properties, such as Michaelis-Menton constants ($K_m$) and/or turnover numbers ($K_{cat}$) relating to a particular substrate provide the basis for evaluating the sensitivity of an enzyme for one or more substrates and provide information regarding the reproducibility of the methods, kits and assays contemplated by the present inventions.

As used herein, the term "intrinsic enzymatic activity" refers to the repeatable reaction which an enzyme catalyzes or causes to occur, for example in the presence of a substrate with which such enzyme is known to react. In one embodiment of the present invention, the intrinsic enzymatic activity of an enzyme may be exploited to confirm the presence or absence of such enzyme in a particular test sample. For example, many enzymes have known and repeatable catalytic activity, which may be enhanced under certain conditions, such as the presence of the appropriate substrate. Intrinsic enzymatic activity may be measured by routine means known to one of ordinary skill in the art (e.g., colorimetric, spectrophotometric, fluorometric or chromatographic assays) by determining, for example the consumption or depletion of substrate and/or the production of a product over time. In accordance with the present invention, substrate depletion of about 5%, 10%, 20%, 30%, 40%, 50% or more, or preferably about 55%, 60%, 65%, 70%, 75%, 80%, 85%, 90%, 95%, 99% or more relative to the amount of substrate introduced may be indicative of intrinsic enzymatic activity. Alternatively, following contacting an enzyme with a substrate, a relative increase in the formation of a product, or the conversion of that substrate to product, in each case of about 5%, 10%, 20%, 30%, 40%, 50% or more, or preferably about 55%, 60%, 65%, 70%, 75%, 80%, 85%, 90%, 95%, 99%, or more preferably 100% or more, may be indicative of intrinsic enzymatic activity.

The methods described herein are useful for development of kits that can be used for the detection of enzymes in a test sample. Such kits include one or more capture agents (e.g., lectins or fusion proteins) fixed on a solid support which are capable of binding to a glycosylated enzyme present in a selected test sample. The kits may also include additional reagents such as buffers, substrates, enzymes, chemicals and other compositions useful for further analysis and/or quantification of the ligand-bound enzyme fraction. Kits can also include components for test sample preparation. The methods and kits described herein are useful for providing a platform for the semi-quantitative assessment of the presence of glycosylated enzymes in a test sample.

While certain compounds, compositions and methods of the present invention have been described with specificity in accordance with certain embodiments, the following examples serve only to illustrate the methods, assays, kits and compositions of the invention and are not intended to limit the same.

The articles "a" and "an" as used herein in the specification and in the claims, unless clearly indicated to the contrary, should be understood to include the plural referents, Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLE 1

Studies performed using the inventions disclosed herein have demonstrated carbohydrate-specific binding of agalsidase alfa and galactocerebrosidase drug substance material to several capture agents. The capture agents evaluated included the biotinylated lectins ConA (specific for core α-mannose structures), WGA (specific for dimers and trimers of N-acetyl-glucosamine), and SNA (specific for Neu5Ac(α2, 6)Gal structures).

Technical Feasibility

To determine the technical feasibility of the methods, assays and compositions described herein, purified agalsidase alfa, aryl sulfatase A and galactocerebrosidase samples were initially assessed. The choice of capture agent was initially limited to only a select few lectins with well defined binding specificities. The lectin capture agents utilized included: (1) concanavalin A (Con A), one of the most commonly used lectins and known to bind avidly to core α-mannose structures of N-linked high-mannose and biantennary complex-type oligosaccharides, (2) *Sambucus nigra* lectin (SNA) and *Maackia amurensis* lectin (MAL), which recognize Neu5Ac(α2, 6)Gal and Neu5Ac(α2, 3)Gal respectively, (3) *Ricinus communis* agglutinin I (RCAI), which binds terminal β1,4-linked Gal, and (4) wheat germ agglutinin (WGA), which binds poly-lactosamine repeats Galβ1, 4GlcNAc. Technical feasibility was based on sensitivity of detection. Feasibility was further evaluated using in-process test samples provided from cell culture/process development streams.

Results

Figure 2:
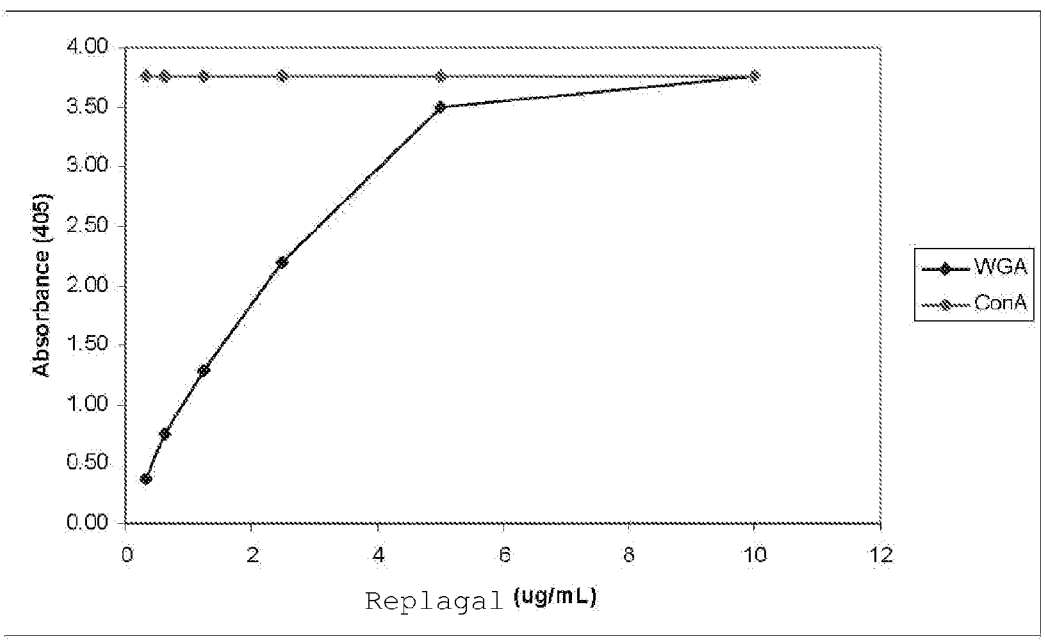
FIG. 2 illustrates binding of agalsidase alfa to immobilized wheat germ agglutinin (WGA) and concanavalin A (ConA) as determined by measuring the enzymatic activity of agalsidase alfa (Replagal®) based on the substrate 4-nitrophenyl-α-D-galactopyranoside.

Method feasibility was evaluated using agalsidase alfa (Replagal®) drug substance and the biotinylated lectins ConA and WGA as the capture agents. The binding of decreasing agalsidase alfa concentrations (40 ug/mL to 300 ng/mL) to the immobilized lectins was analyzed by measuring the enzymatic activity of the bound enzyme. The enzyme activity of agalsidase alfa was determined under steady-state conditions for the synthetic colorimetric substrate 4-nitrophenyl-α-D-galactopyranoside. The substrate was hydrolyzed into 4-nitrophenol and α-D-galactopyranoside where the p-nitrophenol product was read at 405 nm once the reaction was halted with an alkaline buffer. The binding curves of agalsidase alfa (Replagal®) by both WGA and ConA (in absorbance units) are shown in FIG. 2.

The high avidity for ConA (which is specific for α-linked mannose structures) at all concentrations tested demonstrated the high sensitivity of the assays and methods described herein. The binding for WGA (which is specific for dimers and trimers of N-acetyl-glucosamine) was less avid and followed a more classical titration curve. These studies demonstrated the potential of the methods and assays of the present invention in terms of their sensitivity and high-throughput nature.

EXAMPLE 2

Figure 3:
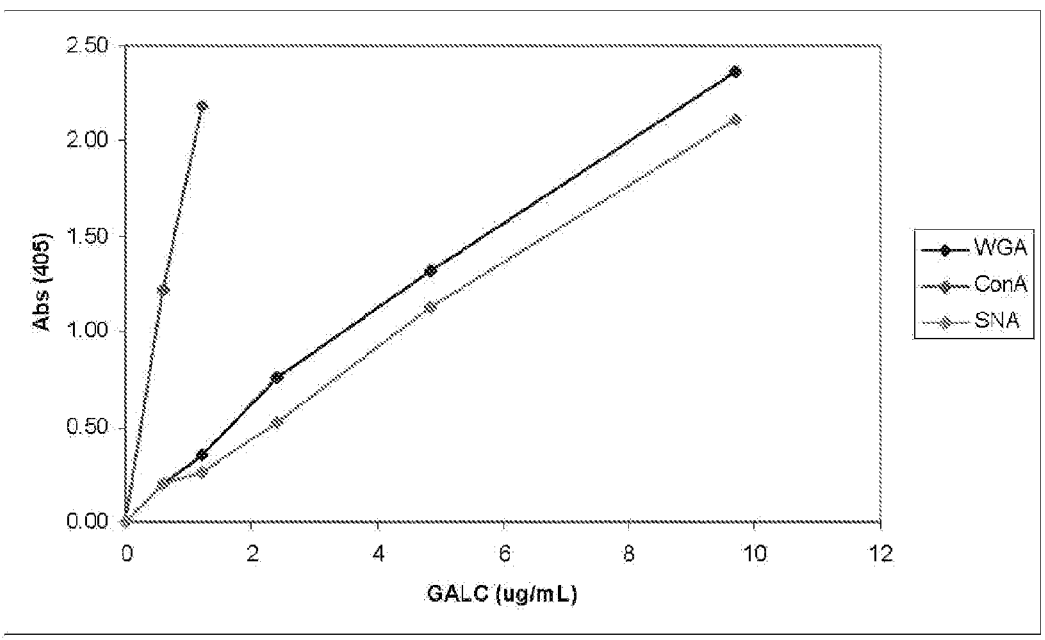
FIG. 3 illustrates binding of galactocerebrosidase (GalC) to immobilized wheat germ agglutinin (WGA), concanavalin A (ConA), and *Sambucus nigra* lectin (SNA) as determined by measuring enzymatic activity of GalC using the substrate 4-nitrophenyl-β-D-galactopyranoside.

Method feasibility was further evaluated with galactocerebrosidase (GalC) drug substance material and the biotinylated lectins concanavalin A (Con A), wheat germ agglutinin (WGA), and *Sambucus nigra* lectin (SNA). The binding curves in FIG. 3 demonstrate both strong and selective binding to GalC.

Figure 4:
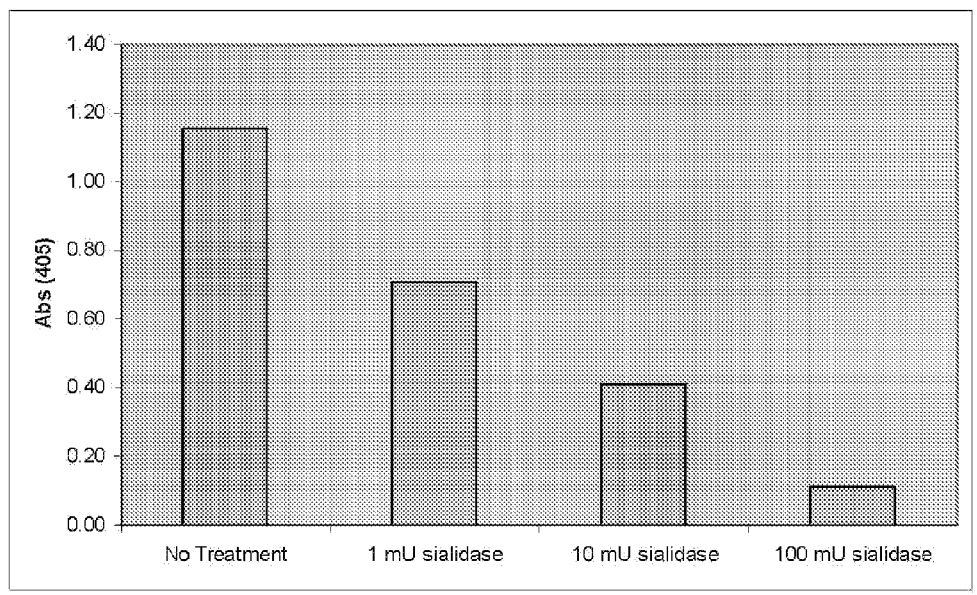
FIG. 4 illustrates binding of galactocerebrosidase (GalC) treated with increasing concentrations of sialidase to immobilized *Sambucus nigra* lectin (SNA), as determined by measuring enzymatic activity of GalC using the substrate 4-nitrophenyl-β-D-galactopyranoside.

To determine whether the methods and assays of the present invention were capable of detecting differences in the amount of GalC-associated sialic acid, GalC samples were subjected to increasing amounts of sialidase pre-treatment and then evaluated for binding. The results provided in FIG. 4 demonstrate that controlled removal of sialic acid results in reduced binding, providing evidence that the assays and methods of the present invention are capable of measuring differences in the amount of GalC-associated sialic acid.

EXAMPLE 3

To confirm the sialic acid binding specificity of *Sambucus nigra* lectin (SNA), aryl sulfatase A drug substance samples produced in CHO and human cells containing approximately 1 mol of sialic acid per mol of protein in either α2,6-linkage (human cell-derived) or α2,3-linkage (CHO cell-derived) were analyzed for binding.

Figure 5:
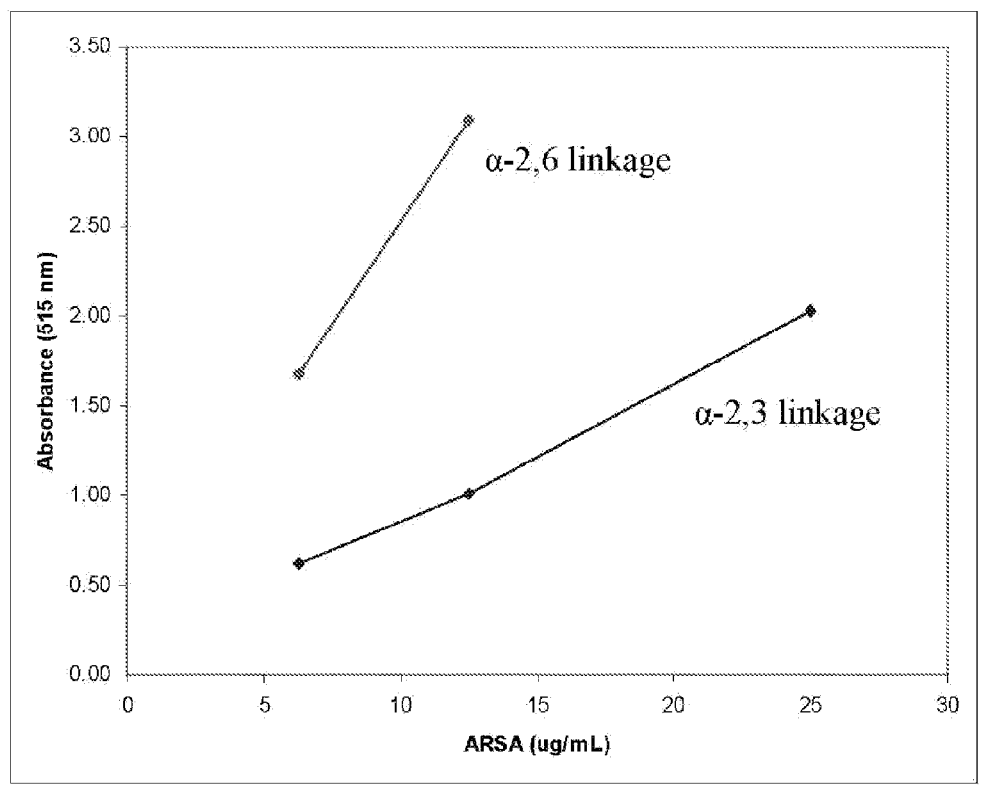
FIG. 5 illustrates linkage-specific binding of purified aryl sulfatase A (ARSA) containing sialic acid in either α-2, 6 or α-2, 3 linkages to *Sambucus nigra* lectin (SNA), as determined by measuring enzymatic activity of ARSA using the substrate p-nitrocatechol sulfate.

The binding curves provided in FIG. 5 illustrate both the selective binding for sialic acid in the α2,6-linkage and the α2,3-linkage.

EXAMPLE 4

To determine whether the assays, methods and compositions described herein could be applied to actual harvest samples, early, middle, and late galactocerebrosidase (GalC) harvest samples (H2, H10, and H17) from an early stage in the development process were analyzed for binding to *Sambucus nigra* lectin (SNA).

Figure 6:
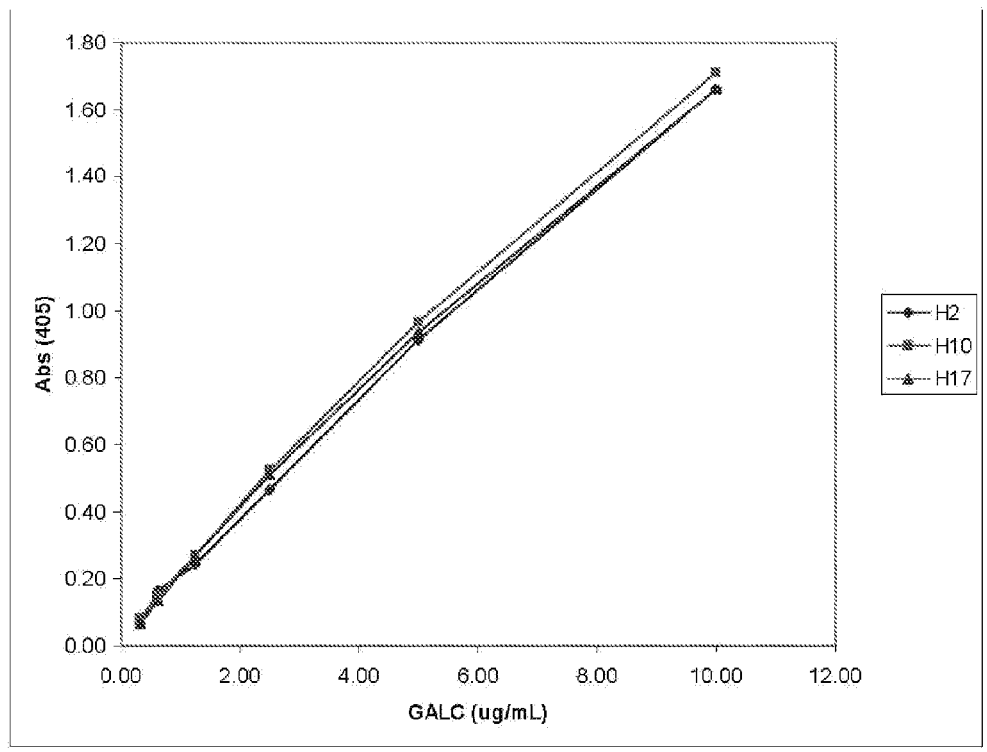
FIG. 6 illustrates binding of galactocerebrosidase (GalC) cell culture from different harvest test samples to *Sambucus nigra* lectin (SNA), as determined by measuring enzymatic activity of GalC using the substrate 4-nitrophenyl-β-D-galactopyranoside.

The results shown in FIG. 6 demonstrate no difference in sialic acid binding across all 3 harvests and importantly validate the intended purpose of the present invention.

EXAMPLE 5

The feasibility of the present invention was also evaluated with aryl sulfatase A drug substance material derived from two different production methods and a recombinant fusion protein which was prepared to function as the capture agent. The recombinant fusion protein consisted of the high affinity binding domain (D9) of the mannose-6-phosphate receptor (M6PR) linked to six histidine residues (6His) to facilitate fixation of the M6PR to a nickel chelate coated solid support. The recombinant fusion protein construct is referred to herein as M6PR(D9)6His and was expressed in HT1080 cells, purified using nickel chelate affinity chromatography, and was affixed onto a 96-well plate.

Figure 7:
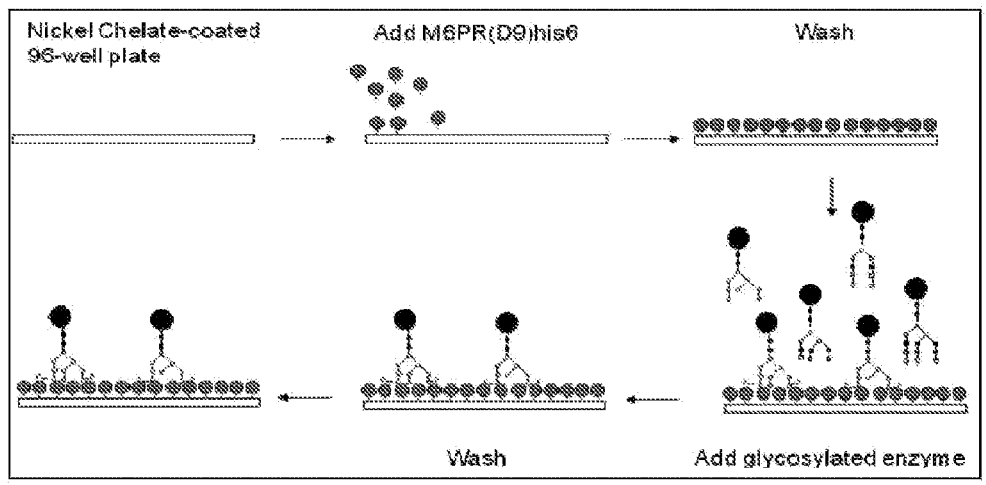
FIG. 7 schematically illustrates one embodiment of the present invention in which the M6PR(D9)6His fusion protein is bound to a nickel chelate-coated 96-well plate, to, which are added test samples containing different preparations of a given glycosylated enzyme which are allowed to bind. Unbound test sample material is then removed by a wash step, and specific detection of the bound enzyme is performed by the addition of the appropriate substrate and assay conditions.

To determine whether the methods and assays of the present invention were capable of detecting differences in the amount of aryl sulfatase A associated M6P associated with the two different production methods, aryl sulfatase A lots with known amounts of M6P were evaluated for binding to immobilized M6PR(D9)6His (FIG. 7). Increasing concentrations of test samples designated as either HGT-1110 or HGT-1111 (corresponding to the respective production methods) were added to the wells and allowed to bind for 2 hours at room temperature. The wells were washed in PBS and the enzyme activity was measured using the substrate p-nitrocatechol sulfate.

Figure 8:
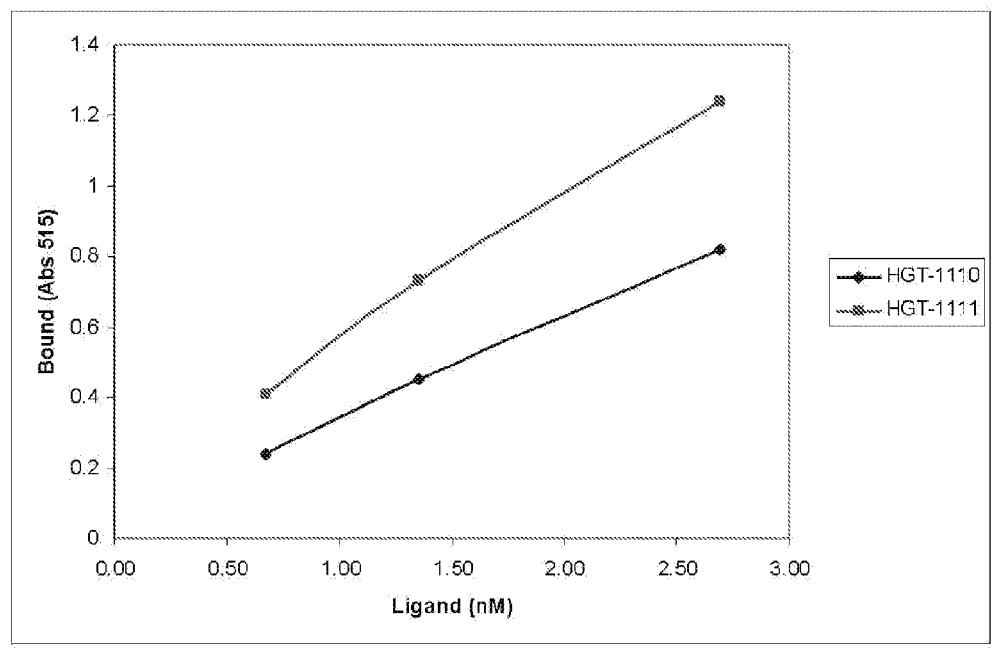
FIG. 8 illustrates detection differences in the amount of aryl sulfatase A (ARSA) associated M6P using ARSA lots with known amounts of M6P.

As shown in FIG. 8, aryl sulfatase A from lot HGT-1111 which known to include more that 2× M6P per mol of protein as compared to aryl sulfatase A from HOT-1111, displayed more avid binding as compared to aryl sulfatase A from lot HGT-1110. These results demonstrate that the methods, assays and kits of the present invention are capable of measuring differences in the amount of aryl sulfatase A-associated M6P.

What is claimed is:

1. A method for detecting the presence of an enzyme in a test sample, wherein said method comprises the steps of: (a) contacting said test sample with at least one capture agent under conditions appropriate for binding of glycosylated enzyme in said test sample to said capture agent, wherein if said glycosylated enzyme is present in said test sample a bound enzyme is formed; (b) separating said bound enzyme from said test sample; and (c) detecting intrinsic enzymatic activity of said bound enzyme, wherein the presence of intrinsic enzymatic activity is indicative of the presence of enzyme in said test sample, and wherein the capture agent comprises a fusion protein.

2. The method of claim 1, wherein said fusion protein comprises at least one mannose-6-phosphate receptor (M6PR) binding domain.

3. The method of claim 1, wherein said fusion protein comprises M6PR binding domain 9.

4. The method of claim 1, wherein said fusion protein comprises six consecutive histidine residues (6His).

5. The method of claim 1, wherein said fusion protein is affixed on a solid support.

6. The method of claim 5, wherein said solid support comprises a metal chelate.

7. The method of claim 5, wherein said solid support comprises a multiple well microtiter plate.

8. The method of claim 5, wherein said solid support comprises at least one bead.

9. The method of claim 1, wherein the step of detecting intrinsic enzymatic activity of said bound enzyme is performed by contacting said bound enzyme with a substrate.

10. The method of claim 9, wherein said substrate is reactive with an enzyme suspected of being present in said test sample.

11. The method of claim 10, wherein said enzyme is agalsidase alfa and said substrate is 4-nitrophenyl-α-D-galactopyranoside.

12. The method of claim 10, wherein said enzyme is galactocerebrosidase and said substrate is 4-nitrophenyl-β-D-galactopyranoside.

13. The method of claim 10, wherein said enzyme is aryl sulfatase A and said substrate is p-nitrocatechol sulfate.

14. The method of claim 10, wherein the step of detecting intrinsic enzymatic activity comprises quantitatively determining the depletion of said substrate.

15. A method for detecting the presence of an enzyme in a test sample, wherein said method comprises the steps of: (a) contacting a test sample with at least one capture agent under conditions appropriate for binding of glycosylated enzyme, wherein if said glycosylated enzyme is present in said test sample a bound enzyme is formed; (b) separating said bound enzyme from said test sample; (c) contacting said bound enzyme with at least one substrate; and (d) detecting the presence or absence of intrinsic enzymatic activity of said bound enzyme, wherein the presence of intrinsic enzymatic activity is indicative of the presence of enzyme in said test sample, and wherein the capture agent comprises a fusion protein.

16. A kit for detecting the presence of glycosylated enzyme in a test sample, wherein said kit comprises (a) at least one capture agent, wherein said capture agent is capable of binding said glycosylated enzyme, and wherein the capture agent comprises a fusion protein, and (b) at least one substrate, wherein said substrate is reactive with said glycosylated enzyme.

17. The method of claim 15, wherein the fusion protein comprises at least one M6PR binding domain.

18. The method of claim 15, wherein the fusion protein comprises M6PR binding domain 9.

19. The method of claim 15, wherein the fusion protein comprises six consecutive histidine residues (6His).

20. The method of claim 15, wherein the fusion protein is affixed on a solid support.

21. The method of claim 20, wherein the solid support comprises a metal chelate.

22. The method of claim 20, wherein the solid support comprises a multiple well microtiter plate.

23. The method of claim 20, wherein the solid support comprises at least one bead.

24. The method of claim 15, wherein the substrate is reactive with an enzyme suspected of being present in the test sample.

25. The method of claim 24, wherein the enzyme is agalsidase alfa and the substrate is 4-nitrophenyl-α-D-galactopyranoside.

26. The method of claim 24, wherein the enzyme is galactocerebrosidase and the substrate is 4-nitrophenyl-β-D-galactopyranoside.

27. The method of claim 24, wherein the enzyme is aryl sulfatase A and the substrate is p-nitrocatechol sulfate.

28. The method of claim 24, wherein the step of detecting intrinsic enzymatic activity comprises quantitatively determining the depletion of the substrate.

29. The kit of claim 16, wherein the fusion protein comprises at least one M6PR binding domain.

30. The kit of claim 16, wherein the fusion protein comprises M6PR binding domain 9.

31. The kit of claim 16, wherein the fusion protein comprises six consecutive histidine residues (6His).

32. The kit of claim 16, wherein the kit further comprises a solid support.

33. The kit of claim 32, wherein the fusion protein is affixed onto the solid support.

34. The kit of claim 32, wherein the solid support comprises a metal chelate.

35. The kit of claim 32, wherein the solid support comprises a multiple well microtiter plate.

36. The kit of claim 32, wherein the solid support comprises at least one bead.

37. The kit of claim 16, wherein the glycosylated enzyme is selected from the group consisting of aryl sulfatase A, agalsidase alfa and galactocerebrosidase.

38. The kit of claim 16, wherein the substrate is selected from the group consisting of 4-nitrophenyl-α-D-galactopyranoside, 4-nitrophenyl-β-D-galactopyranoside and para-nitrocatechol sulfate.

39. The kit of claim 16, wherein the glycosylated enzyme is agalsidase alfa, and the substrate is 4-nitrophenyl-α-D-galactopyranoside.

40. The kit of claim 16, wherein the glycosylated enzyme is galactocerebrosidase, and the substrate is 4-nitrophenyl-β-D-galactopyranoside.

41. The kit of claim 16, wherein the glycosylated enzyme is aryl sulfatase A, and the substrate is p-nitrocatechol sulfate.

42. The kit of claim 16, wherein the kit further comprises a component to separate the bound enzyme from the test sample.

* * * * *